US012758263B2

(12) United States Patent
Khan

(10) Patent No.: US 12,758,263 B2
(45) Date of Patent: Oct. 13, 2026

(54) OBSTETRICIAN ASSISTANCE DEVICE AND METHOD TO OPERATE THE SAME

(71) Applicant: Mutarba Altaf Khan, Mumbai (IN)

(72) Inventor: Mutarba Altaf Khan, Mumbai (IN)

(73) Assignee: Mutarba Altaf Khan, Mumbai (IN)

( * ) Notice: Subject to any disclaimer, the term of this patent is extended or adjusted under 35 U.S.C. 154(b) by 23 days.

(21) Appl. No.: 19/111,358

(22) PCT Filed: Nov. 2, 2022

(86) PCT No.: PCT/IB2022/060549
§ 371 (c)(1),
(2) Date: Mar. 13, 2025

(87) PCT Pub. No.: WO2024/057082
PCT Pub. Date: Mar. 21, 2024

(65) Prior Publication Data

US 2026/0083477 A1 Mar. 26, 2026

(30) Foreign Application Priority Data

Sep. 16, 2022 (IN) ............................ 202221053108

(51) Int. Cl.
*A61B 17/44* (2006.01)
*A61B 17/00* (2006.01)

(52) U.S. Cl.
CPC .. *A61B 17/442* (2013.01); *A61B 2017/00367* (2013.01); *A61B 2017/00557* (2013.01)

(58) Field of Classification Search
CPC ........ A61B 17/442; A61B 2017/00557; A61B 2017/00367
See application file for complete search history.

(56) References Cited

U.S. PATENT DOCUMENTS

| | | | | |
|---|---|---|---|---|
| 5,507,752 | A | 4/1996 | Elliott | |
| 9,055,973 | B2 | 6/2015 | Varma | |
| 9,247,958 | B2 * | 2/2016 | Odon | A61B 17/42 |
| 11,090,084 | B2 * | 8/2021 | Varma | A61B 17/442 |
| 11,096,626 | B2 * | 8/2021 | Recanati | A61B 5/0011 |
| 2003/0229372 | A1 * | 12/2003 | Reiley | A61F 2/4601 606/192 |
| 2008/0269773 | A1 * | 10/2008 | George | A61B 17/442 606/123 |
| 2009/0254096 | A1 * | 10/2009 | Porat | A61B 5/4362 600/300 |

(Continued)

*Primary Examiner* — Phong Song H Dang
(74) *Attorney, Agent, or Firm* — Jason C. Cameron

(57) ABSTRACT

An obstetrician assistance device 100 is provided. The device includes a clasping assembly 102 comprising a holding structure 104 to hold a protruding part of a foetus, a base 106 to support the holding structure and a tube 108 connected to the base. The device also includes a rod 110 detachably connected to the base comprising a front-end portion 110*a* connected to the base and a rear-end portion 110*b*, a working element 112 disposed moveably inside the rod and a handle arrangement 114 operatively coupled with the clasping assembly via the rod. The handle arrangement includes a handle 116, a lock 118 disposed on the handle, a trigger 120 disposed inside the handle and connected to the working element via a connecting element 122. The working element is actuated by the trigger and elevate the protruding part of the foetus, thereby preventing pressure by the foetus on an umbilical cord.

10 Claims, 3 Drawing Sheets

(56) References Cited

U.S. PATENT DOCUMENTS

| | | | | |
|---|---|---|---|---|
| 2010/0324568 | A1* | 12/2010 | Varma | A61B 17/442 606/121 |
| 2011/0190781 | A1* | 8/2011 | Collier | A61B 17/00234 606/114 |
| 2012/0083660 | A1* | 4/2012 | Okoniewski | A61B 17/0293 600/207 |
| 2014/0188126 | A1* | 7/2014 | Odon | A61B 17/442 606/122 |
| 2017/0065298 | A1 | 3/2017 | Harris | |
| 2018/0206886 | A1* | 7/2018 | Beaven | A61B 17/442 |
| 2019/0142467 | A1 | 5/2019 | Varma | |

* cited by examiner

OBSTETRICIAN ASSISTANCE DEVICE AND METHOD TO OPERATE THE SAME

EARLIEST PRIORITY DATE

This Application claims priority from a complete patent application filed in India having Patent Application No. 202221053108, filed on Sep. 16, 2022, and titled "OBSTETRICIAN ASSISTANCE DEVICE AND METHOD TO OPERATE THE SAME" and a PCT Application no. PCT/IB2022/060549 filed on Nov. 2, 2022, and titled "OBSTETRICIAN ASSISTANCE DEVICE AND METHOD TO OPERATE THE SAME"

FIELD OF INVENTION

Embodiments of a present disclosure relate to field of obstetrics, and more particularly to an obstetrician assistance device and method to operate the same.

BACKGROUND

An umbilical cord in human is a tube-like structure connecting a developing foetus and a placenta. The umbilical cord is generally 50 cm long and having diameter of 2 cm. The umbilical cord carries the baby's blood back and forth, between the baby and the placenta. The umbilical cord carried oxygen and nutritious food to foetus from the placenta. The umbilical cord has high importance in developing foetus. The umbilical cord problems can cause serious threat to child's health. The umbilical cord related problems occurred during childbirth are, umbilical cyst, the cord is too long or short, cord prolapse and the like. The umbilical cord prolapse is a condition when umbilical cord comes out of uterus. The pressure on cord from baby, minimises blood flow and oxygen to the baby. There are many risk factors related to cord prolapse like crippled baby, cerebral palsy, and the like. Thus, the risk of mental and physical health will be for life and thus increasing the cost of living greatly for the parents. The treatments available in condition of cord prolapse are repositioning of the mother, like knee-chest position, taking medicines or immediate caesarean section.

The currently used techniques are inefficient for managing cord prolapse and related problems. The consequence of emergency caesarean section is a crippled baby. Other manoeuvres like repositioning of mother, manual elevation of the protruding foetal part is not supported by doctors as there is insufficient evidence to support such manoeuvres. Further, doctors manually elevate the presenting part by lifting the presenting part off the cord by vaginal examination. Manual elevation of foetal presenting part has risk factors that the manual elevation if not done carefully and smoothly the presenting part of fetus may get harmed and cord may get compressed. Also, the manual elevation is a painful process for patient. Also, in existing techniques, time required to elevate the presenting part of fetus is high, such that the obstetricians may not get ample amount of time to prepare for a cesarean section.

Hence, there is a need for an improved device and method for assisting the obstetrician which addresses the aforementioned issues.

BRIEF DESCRIPTION

In accordance with one embodiment of the disclosure, an obstetrician assistance device is provided. The device includes a clasping assembly, a handle arrangement, a rod, and a working element. The clasping assembly includes a holding structure adapted to hold a protruding part of a foetus in an operating position. The holding structure being adapted to inflate and deflate for securely holding and releasing the protruding part of the foetus. The clasping assembly also includes a base adapted to support the holding structure in the operating position. The clasping assembly further includes a tube connected to the base for inflating and deflating the holding structure. The rod detachably connected to the base. The rod includes a front-end portion and a rear end portion. The front-end portion of the rod is connected to the base. The working element disposed moveably inside the rod. The working element is connected to the holding structure and projecting from the rear end portion of the rod.

The handle arrangement operatively coupled with the clasping assembly via the rod. The handle arrangement includes, a handle, a lock disposed on the handle to lock the holding structure in the operating position and prevent movement of the protruding part of the foetus. The handle arrangement also includes a trigger disposed inside the handle and connected to the working element via a connecting element. The trigger is adapted to enable the working element to be actuated to elevate the protruding part of the foetus and lock the holding structure to prevent movement of foetus and thereby preventing pressure on an umbilical cord by the foetus.

In accordance with another embodiment, a method for providing an obstetrician assistance device is provided. The method includes providing, a clasping assembly. Also, the method includes holding, by a holding structure, a protruding part of a foetus in an operating position, where the holding structure being adapted to inflate and deflate for securely holding and releasing the protruding part of the foetus. Further, the method includes supporting, by a base, the holding structure in the operating position. Furthermore, the method includes inflating and deflating, by a tube, the holding structure. Moreover, the method includes connecting the base with a rod, where the rod includes a front-end portion and a rear end portion, where the front-end portion detachably connected to the base. Additionally, the method includes providing, a working element, disposed moveably inside the rod, where the working element is connected to the holding structure and projecting from the rear end portion of the rod. Furthermore, the method also includes providing a handle arrangement, operatively coupled with the clasping assembly via the rod. The method includes locking, by a lock, the holding structure in the operating position and prevent movement of the protruding part of the foetus. The method also includes actuating the working element, by a trigger, for elevating the protruding part of the foetus and locking the holding structure to prevent movement of the foetus and thereby preventing pressure on an umbilical cord by the foetus.

To further clarify the advantages and features of the present disclosure, a more particular description of the disclosure will follow by reference to specific embodiments thereof, which are illustrated in the appended figures. It is to be appreciated that these figures depict only typical embodiments of the disclosure and are therefore not to be considered limiting in scope. The disclosure will be described and explained with additional specificity and detail with the appended figures.

BRIEF DESCRIPTION OF THE DRAWINGS

The disclosure will be described and explained with additional specificity and detail with the accompanying figures in which.

Further, those skilled in the art will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those skilled in the art having the benefit of the description herein.

DETAILED DESCRIPTION

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications in the illustrated system, and such further applications of the principles of the disclosure as would normally occur to those skilled in the art are to be construed as being within the scope of the present disclosure.

The terms “comprises”, “comprising”, or any other variations thereof, are intended to cover a non-exclusive inclusion, such that a process or method that comprises a list of steps does not include only those steps but may include other steps not expressly listed or inherent to such a process or method. Similarly, one or more devices or sub-systems or elements or structures or components preceded by “comprises . . . a” does not, without more constraints, preclude the existence of other devices, sub-systems, elements, structures, components, additional devices, additional sub-systems, additional elements, additional structures or additional components. Appearances of the phrase “in an embodiment”, “in another embodiment” and similar language throughout this specification may, but not necessarily do, all refer to the same embodiment.

Unless otherwise defined, all technical and scientific terms used herein have the same meaning as commonly understood by those skilled in the art to which this disclosure belongs. The system, methods, and examples provided herein are only illustrative and not intended to be limiting.

In the following specification and the claims, reference will be made to a number of terms, which shall be defined to have the following meanings. The singular forms “a”, “an”, and “the” include plural references unless the context clearly dictates otherwise.

Embodiments of the present disclosure relate to an obstetrician assistance device. As used herein, the term “obstetrician assistance” defined as an assistance provided to an obstetrician by providing surgical care for woman, specifically in situations like umbilical cord prolapse. Further, the device described hereafter in FIG. 1 is the obstetrician assistance device.

Figure 1:
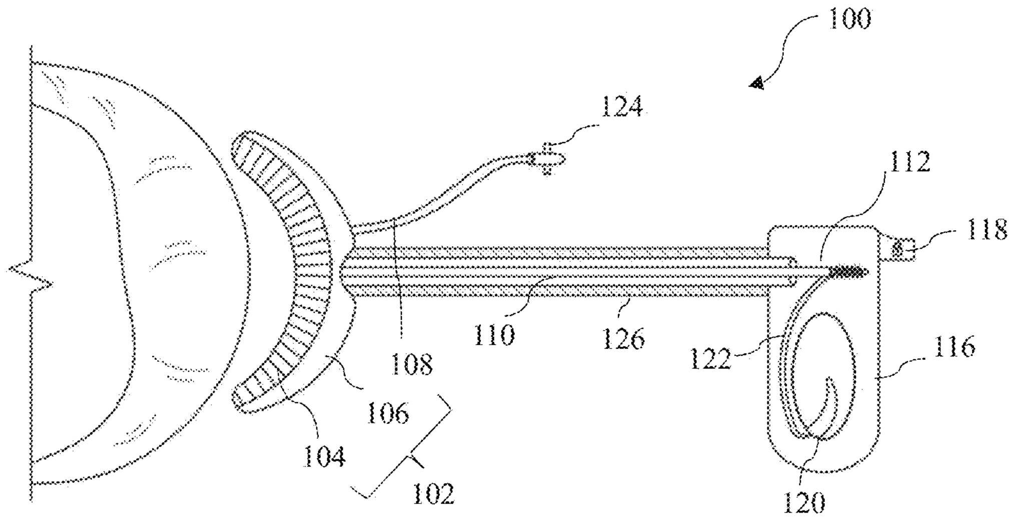
FIG. 1 is schematic representation of an obstetrician assistance device in accordance with an embodiment of the present disclosure.

FIG. 1 is schematic representation of an obstetrician assistance device (100) in accordance with an embodiment of the present disclosure. The device 100 includes a clasping assembly 102, a rod 110, a working element 112 and a handle arrangement 114.

The clasping assembly 102 includes a holding structure 104, a base 106 and a tube 108. The holding structure 104 is adapted to hold a protruding part of a foetus in an operating position. In one embodiment, the ‘operating position’ of the device is the position when the device securely holds the protruding part of the foetus for elevating the protruding part. In one embodiment, the protruding part of the foetus may be a body part of foetus whose pressure may be exerted on an umbilical cord. The body part of foetus may be a head, legs, and the like. In one embodiment, the ‘umbilical cord’ is a tube-like structure which is flexible and during pregnancy the cord connects the foetus to placenta. The holding structure 104 is adapted to inflate and deflate for securely holding and releasing the protruding part of the foetus. Accordingly, in one embodiment, the holding structure 104 is inflatable in the operating position and deflate in a non-operative position. In another embodiment, the holding structure 104 may be made up of a material such as, but not limited to, silicon, rubber, and plastic. In one embodiment, the holding structure may be inflated by air pressure or by inserting saline into the holding structure 104.

The base 106 is adapted to support the holding structure 102 in the operating position. In one embodiment, the base 106 may be a foldable firm base adapted to support the holding structure 102. The tube 108 is connected to the base 106 for inflating and deflating the holding structure 104. In one embodiment, the tube 108 includes a two-way knob 124 connected to a source of pressurized air. The two-way knob facilitates controlled inflation and deflation of the holding structure 104. In another embodiment, the tube 108 may be made of a rubber which is elastic in nature.

The rod 110 is detachably connected to the base 106, where the rod 110 includes a front-end portion 110 *a* and a rear end portion 110 *b*. The front-end portion of the rod 110*a* is connected to the base 106. In one embodiment, the rod 110 may be a metal rod and connected to the clasping assembly 102 via one or more screws. In another embodiment, the rod 110 may be cylindrical in shape. Further, in one embodiment, the rod 110 may be covered by an insulation material 126 for preventing cooling of the rod 110, thereby preventing muscle contraction of the lady. In one embodiment, the insulation material 126 may be made of rubber.

The working element 112 is disposed moveably inside the rod 110, where the working element 112 is connected to the holding structure 104 and projecting from the rear end portion 110*b* of the rod 110. In one embodiment, the working element 112 is cylindrical in shape. In another embodiment, the diameter of working element 112 is less than the diameter of rod 110 and length of working element 112 is greater than length of the rod 110.

The handle arrangement 114 includes a handle 116, a lock 118 and a trigger 120. The handle arrangement 114 is operatively coupled with the clasping assembly 102 via the rod. The handle arrangement 114 includes a handle 116 which may hold the device in the operative position.

The handle arrangement 114 also includes a lock 118 which is disposed on the handle 116 to lock the holding structure 104 in the operating position and prevent movement of the protruding part of the foetus. In on embodiment, the lock 118 may be a push/pull arrangement. In another embodiment, the lock may be made up of material including rubber or metal. However, the present disclosure is not limited to any material of lock.

The trigger 120 is disposed inside the handle 116 and connected to the working element 112 via a connecting element 122. The trigger 120 is adapted to enable the working element 112 to be actuated to elevate the protruding part of the foetus, and lock 118 the holding structure 104 to prevent movement of foetus and thereby preventing pressure on an umbilical cord by the foetus. In one embodiment, the connecting element 122 may be a string or a spring or both.

Figure 2:
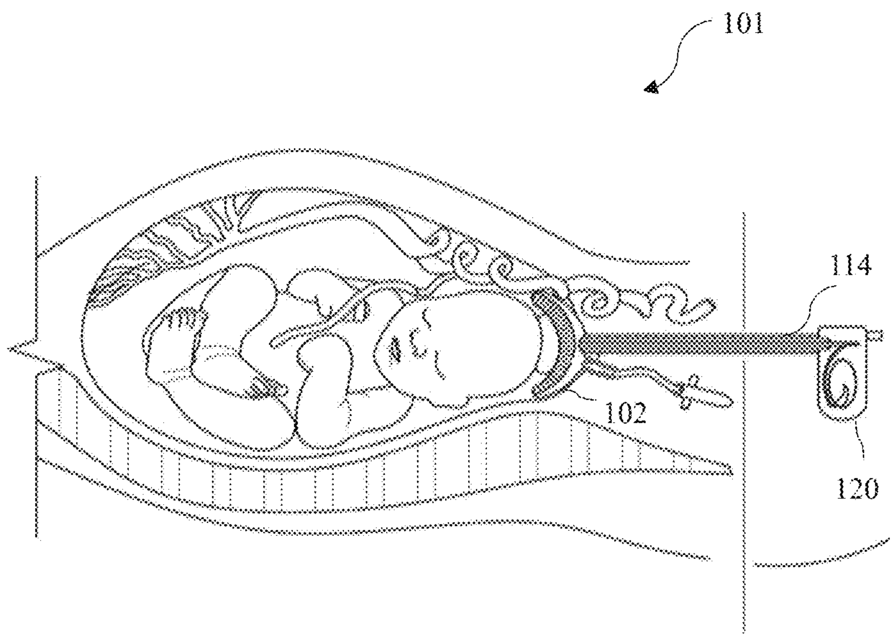
FIG. 2 is a schematic representation of an embodiment of the obstetrician assistance device in operating position of FIG. 1 in accordance with an embodiment of the present disclosure.

FIG. 2 illustrates schematic representation of one embodiment 101 of the device 100 of FIG. 1 in the operating position, in accordance with an embodiment of the present disclosure. In an exemplary embodiment, the protruding part of foetus may be head. The holding structure is inflated with the help of the tube. In one embodiment, the holding structure is air inflated. The air pressure of the holding structure may be 90 bar/Psi/mm. In another embodiment, the holding structure 104 may be inflated via saline water. The holding structure securely holds the foetus head. The working element 112, which is movable inside the rod 110, when actuated via the connecting element 122 the head of the foetus gets elevated. The lock 118 is disposed on the handle 116, locks the device and thereby the head of the foetus is locked in elevated position. Thus, the elevated position of foetus prevents pressure on umbilical cord and hence giving time for obstetricians to prepare for caesarean section.

Figure 3:
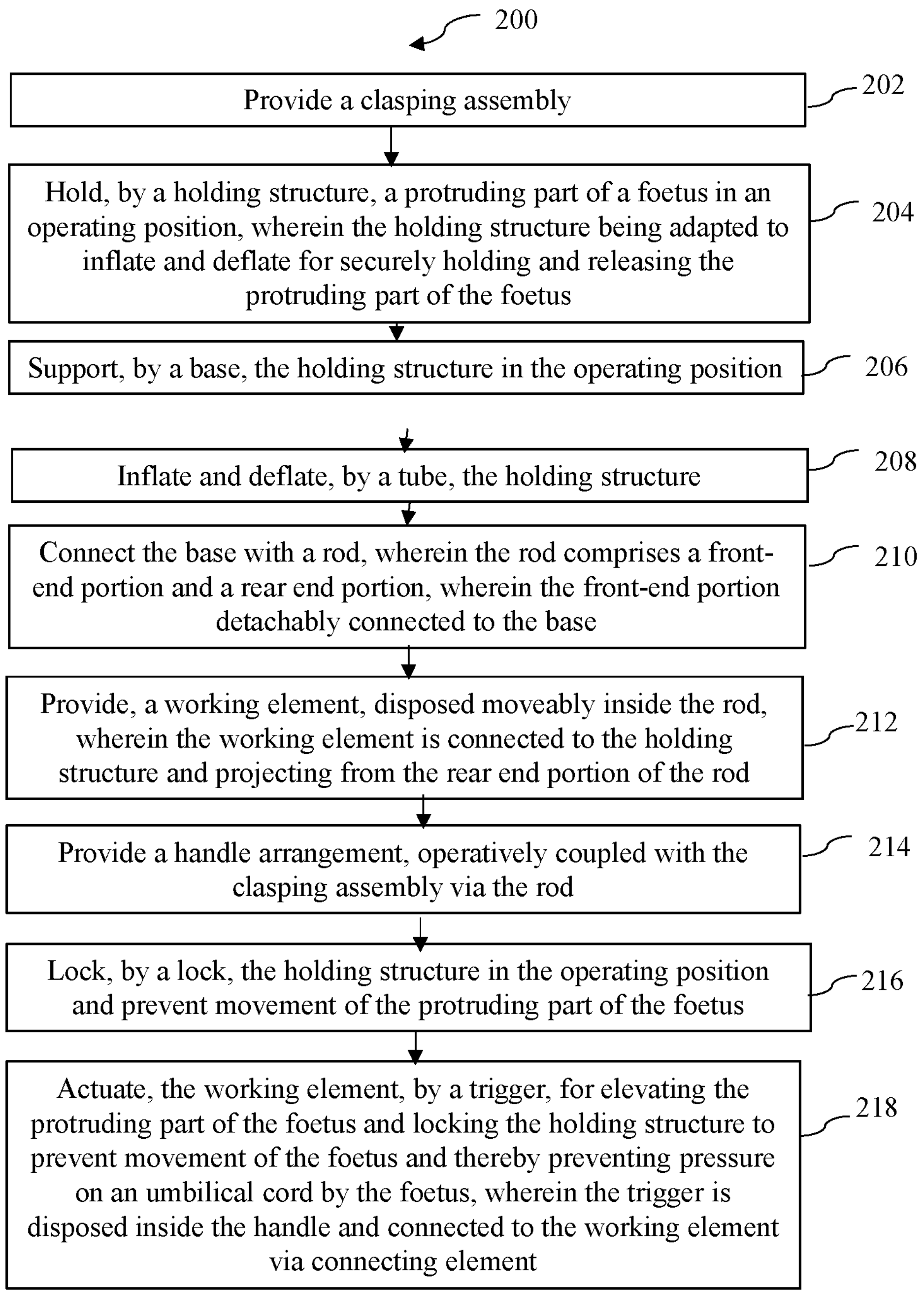
FIG. 3 is a flow chart representing steps involved in a method for providing an obstetrician assistance device in accordance with an embodiment of the present disclosure.

FIG. 3 is a flow chart representing steps involved in a method 200 for providing an obstetrician assistance device in accordance with an embodiment of the present disclosure. The method 200 includes providing, a clasping assembly 202.

The method 200 also includes holding, by a holding structure, a protruding part of a foetus in an operating position, where the holding structure being adapted to inflate and deflate for securely holding and releasing the protruding part of the foetus in step 204. In one embodiment, inflating in the operative position and deflating in non-operative position. In another embodiment, making, the holding structure by at least of one of silicon, rubber, and plastic.

Furthermore, the method 200 also includes supporting, by a base, the holding structure in the operating position in step 206. In one embodiment, supporting, by a foldable firm base, to support the holding structure.

Furthermore, the method 200 also includes inflating and deflating, by a tube, the holding structure in step 208. In one embodiment, consisting, a two-way knob connected to a source of pressurized air, where the two-way knob facilitates controlled inflation and deflation of the holding structure.

Furthermore, the method 200 also includes connecting the base with a rod, where the rod comprises a front-end portion and a rear end portion, where the front-end portion detachably connected to the base in step 210. In one embodiment, covering rod by an insulation material for preventing cooling of the rod, thereby preventing muscle contraction of the patient. In another embodiment, connecting, a metal rod, by the rod, to the clasping assembly via one or more screws Furthermore, the method 200 also includes providing, a working element, disposed moveably inside the rod, where the working element is connected to the holding structure and projecting from the rear end portion of the rod in step 212.

Furthermore, the method 200 also includes providing a handle arrangement, operatively coupled with the clasping assembly via the rod in step 214. Furthermore, the method 200 also includes locking, by a lock, the holding structure in the operating position and prevent movement of the protruding part of the foetus in step 216.

Furthermore, the method 200 also includes actuating the working element, by a trigger, for elevating the protruding part of the foetus and locking the holding structure to prevent movement of the foetus and thereby preventing pressure on an umbilical cord by the foetus, where the trigger is disposed inside the handle and connected to the working element via connecting element in step 218. In one embodiment, the method includes providing, the connecting element, such as at least one of a string and a spring.

Various embodiments of the present disclosure provide a device for assisting obstetrician in critical situation like umbilical cord prolapse. The present disclosure reduces risk of damaging the foetal protruding part or compression of umbilical cord, by avoiding manual elevation of protruding part of foetus. Further, by using the device of the present disclosure, the protruding part of foetus get elevated smoothly and painlessly. In the situation of cord prolapse, immediate caesarean section is required, thus by using the device, doctors may get ample amount of time to prepare for caesarean section. The device of the present disclosure is easy to use and does not require any battery or external electric supply.

While specific language has been used to describe the disclosure, any limitations arising on account of the same are not intended. As would be apparent to a person skilled in the art, various working modifications may be made to the method in order to implement the inventive concept as taught herein.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, order of processes described herein may be changed and are not limited to the manner described herein. Moreover, the actions of any flow diagram need not be implemented in the order shown; nor do all of the acts need to be necessarily performed. Also, those acts that are not dependent on other acts may be performed in parallel with the other acts. The scope of embodiments is by no means limited by these specific examples.

I claim:

1. An obstetrician assistance device, wherein the device comprising:

- a clasping assembly comprising:
  - a holding structure adapted to hold a protruding part of a foetus in an operating position, wherein the holding structure being adapted to inflate and deflate for securely holding and releasing the protruding part of the foetus;
  - a base adapted to support the holding structure in the operating position; and
  - a tube connected to the base for inflating and deflating the holding structure;
- a rod detachably connected to the base, wherein the rod comprising a front-end portion and a rear end portion, wherein the front-end portion of the rod is connected to the base;
- a working element disposed moveably inside the rod, wherein the working element is connected to the holding structure and projecting from the rear end portion of the rod; and
- a handle arrangement operatively coupled with the clasping assembly via the rod, wherein the handle arrangement comprising:
  - a handle;

a lock disposed on the handle to lock the holding structure in the operating position and prevent movement of the protruding part of the foetus; and a trigger disposed inside the handle and connected to the working element via a connecting element, wherein the trigger is adapted to enable the working element to be actuated to elevate the protruding part of the foetus, and lock the holding structure to prevent movement of foetus and thereby preventing pressure on an umbilical cord by the foetus.

2. The device as claimed in claim 1, wherein the holding structure is inflatable in the operating position and deflate in a non-operative position.

3. The device as claimed in claim 1, wherein the holding structure is made of a material comprising at least of one of silicon, rubber, and plastic.

4. The device as claimed in claim 1, wherein the base comprises a foldable firm base to support the holding structure.

5. The device as claimed in claim 1, wherein in the tube comprises a two-way knob connected to a source of pressurized air, wherein the two-way knob facilitates controlled inflation and deflation of the holding structure.

6. The device as claimed in claim 1, wherein the rod is covered by an insulation material for preventing cooling of the rod thereby preventing muscle contraction of the patient.

7. The device as claimed in claim 6, wherein the insulation material comprises rubber.

8. The device as claimed in claim 1, wherein the rod comprises a metal rod and connected to the clasping assembly via one or more screws.

9. The device as claimed in claim 1, wherein the connecting element comprises at least one of a string and a spring.

10. A method for operating obstetrician assistance device comprising:

providing, a clasping assembly;

holding, by a holding structure, a protruding part of a foetus in an operating position, wherein the holding structure being adapted to inflate and deflate for securely holding and releasing the protruding part of the foetus;

supporting, by a base, the holding structure in the operating position;

inflating and deflating, by a tube, the holding structure;

connecting the base with a rod, wherein the rod comprises a front-end portion and a rear end portion, wherein the front-end portion detachably connected to the base;

providing, a working element, disposed moveably inside the rod, wherein the working element is connected to the holding structure and projecting from the rear end portion of the rod;

providing a handle arrangement, operatively coupled with the clasping assembly via the rod;

locking, by a lock, the holding structure in the operating position and prevent movement of the protruding part of the foetus; and actuating the working element, by a trigger, for elevating the protruding part of the foetus and locking the holding structure to prevent movement of the foetus and thereby preventing pressure on an umbilical cord by the foetus, wherein the trigger is disposed inside the handle and connected to the working element via a connecting element.

* * * * *